(12) United States Patent
Morita et al.

(10) Patent No.: US 7,534,904 B2
(45) Date of Patent: May 19, 2009

(54) SILICON-CONTAINING COMPOUND, COMPOSITION CONTAINING SAID COMPOUND, AND INSULATING MATERIAL

(75) Inventors: Kensuke Morita, Shizuoka (JP); Morio Yagihara, Saitama (JP); Koji Wariishi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 615 days.

(21) Appl. No.: 11/138,352

(22) Filed: May 27, 2005

(65) Prior Publication Data

US 2005/0267308 A1    Dec. 1, 2005

(30) Foreign Application Priority Data

May 31, 2004    (JP)    ............... P.2004-161361
Mar. 16, 2005    (JP)    ............... P.2005-075136

(51) Int. Cl.
*C07F 7/18*    (2006.01)

(52) U.S. Cl. ..................................... 556/401

(58) Field of Classification Search ................. 556/401
See application file for complete search history.

(56) References Cited

U.S. PATENT DOCUMENTS

2003/0180550 A1    9/2003    Hara et al.

FOREIGN PATENT DOCUMENTS

EP    0 598 361 A1    5/1994
JP    2000-302791 A    10/2000

*Primary Examiner*—Elvis O Price
(74) *Attorney, Agent, or Firm*—Sughrue Mion, PLLC

(57) ABSTRACT

A composition for forming an insulating film comprising at least one of a compound represented by formula (1), a hydrolysate of the compound represented by formula (1) and a condensate of the compound represented by formula (1):

$$A_nSiX_{(4-n)} \tag{1}$$

wherein n represents an integer of from 1 to 3; A represents an optionally substituted group containing a cage structure formed by 11 or more carbon atoms, and when n represents an integer of 2 or 3, A's are mutually same or different; and X represents a hydrolyzable group, and when n represents an integer of 1 or 2, X's are mutually same or different.

5 Claims, No Drawings

SILICON-CONTAINING COMPOUND, COMPOSITION CONTAINING SAID COMPOUND, AND INSULATING MATERIAL

BACKGROUND OF THE INVENTION

1. Field of the Invention

The present invention relates to a silicon-containing compound which is useful for the formation of insulating materials such as insulating films. In more detail, the invention relates to a composition for forming an insulating film which can form a coating film having a uniform thickness suitable as an interlaminar insulating film material in semi-conductor devices, etc., hardly generates cracks, and is excellent in dielectric constant characteristics, etc.

2. Description of the Related Art

As interlaminar insulating films in semi-conductor devices, etc., there have hitherto been frequently used silica ($SiO_2$) films formed by the vacuum process such as the chemical vapor deposition (CVD) method. In recent years, for the purpose of forming a more uniform interlaminar insulating film, coating type insulating films containing a hydrolysis product of a tetraalkoxysilane as the major component, which are called as "SOG (spin-on-glass) film", are also used. Also, following the progress of high integration of semi-conductors, etc., low dielectric constant interlaminar insulating films containing a polyorganosiloxane as the major component, which are called as organic SOG, are developed.

Also, there is attempted a method for coping with both heat resistance and low dielectric constant by introducing an adamantly group on siloxane (see JP-A-2000-302791).

However, following the progress of higher integration and multi-layered structure, more excellent electrical insulating properties between conductors are required, and interlaminar insulating film materials having a lower dielectric constant and having excellent crack resistance, heat resistance and resistance to chemical mechanical polishing (CMP) are required.

SUMMARY OF THE INVENTION

An object of the invention is to solve the foregoing problems of the related technologies and to provide a composition capable of forming an insulating film having a low relative dielectric constant of not more than 2.4 and having high reliability.

It has been found that the foregoing object of the invention can be achieved by the following means.

(1) A composition for forming an insulating film comprising at least one of a compound represented by formula (1), a hydrolysate of the compound represented by formula (1) and a condensate of the compound represented by formula (1):

$$A_n SiX_{(4-n)} \quad (1)$$

wherein n represents an integer of from 1 to 3;

A represents an optionally substituted group containing a cage structure formed by 11 or more carbon atoms, and when n represents an integer of 2 or 3, A's are mutually same or different; and X represents a hydrolyzable group, and when n represents an integer of 1 or 2, X's are mutually same or different.

(2) The composition as described in (1) above, wherein A('s) contains a diamantyl group.

(3) An insulating film formed from a composition for forming an insulating film as described in (1) or (2) above.

(4) A silicon oxygen crosslinked compound obtained by hydrolyzing and condensing a compound represented by formula (2):

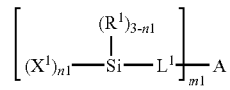

wherein $m_1$ represents an integer of 2 or more;

$n_1$ represents an integer of from 1 to 3;

$X^1$ represents a hydrolyzable group, when $n_1$ represents an integer of 2 or 3, $X^1$'s are mutually same or different;

$R^1$ represents an alkyl group, an aryl group, or a heterocyclic group, when $n_1$ represents an integer of 1, $R^1$'s are mutually same or different;

$L^1$ represents a divalent connecting group; and

A represents a group containing a cage structure formed by 11 or more carbon atoms.

(5) The silicon oxygen crosslinked compound as described in (4) above, wherein A contains a diamantyl group.

(6) A compound represented by formula (3):

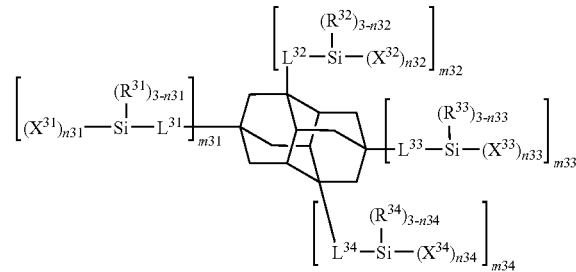

wherein $(m_{31}+m_{32}+m_{33}+m_{34})$ represents an integer of from 1 to 4;

$n_{31}$ to $n_{34}$ each independently represents an integer of from 1 to 3;

$X^{31}$ to $X^{34}$ each independently represents a hydrolyzable group;

$R^{31}$ to $R^{34}$ each independently represents an alkyl group, an aryl group or a heterocyclic group; and $L^{31}$ to $L^{34}$ each independently represents an alkylene, a vinylene, an arylene, —O—, —S—, —CO—, —NR'— or a divalent group including a combination thereof; and R' represents a hydrogen atom, an alkyl group or an aryl group.

(7) The compound as described in (6) above, wherein $L^{31}$ to $L^{34}$ each independently represents an ethylene or a vinylene.

(8) The compound as described in (6) or (7) above, wherein $(m_{31}+m_{32}+m_{33}+m_{34})$ represents 2.

(9) A composition comprising:

a compound represented by formula (2) as described in (4) above;

at least one of a hydrolysate of the compound represented by formula (2) and a condensate of the compound represented by formula (2); and at least one of an organic solvent and a water.

(10) A composition comprising:
a compound represented by formula (3) as described in (6) above;
at least one of a hydrolysate of the compound represented by formula (3) and a condensate of the compound represented by formula (3); and
at least one of an organic solvent and a water.

(11) An insulating material formed by using a composition as described in (9) or (10) above.

(12) An insulating film formed by using a composition as described in (9) or (10) above.

DETAILED DESCRIPTION OF THE INVENTION

As described previously, the composition for forming an insulating film of the invention comprises a silane compound represented by the general formula (1) (hereinafter referred to as "silane compound (1)"). By using this composition, it is possible to impart a very low relative dielectric constant of not more than 2.4 and high reliability to the resulting insulating film.

In the general formula (1), A represents a group containing a cage structure formed by 11 or more carbon atoms (cage structure-containing group). The cage structure-containing group may be a monovalent group of the cage structure itself.

The term "cage structure" as referred to herein is a structure in which the volume is defined by plural rings formed by covalently bonded atoms, and the point positioning in the volume cannot leave from the volume unless it passes through the ring.

For example, an adamantly structure is considered to be a cage structure. In contrast, a cyclic structure containing a single crosslinking such as norbornane (bicyclo[2,2,1]-heptane) is not considered to be a cage structure because the ring of a singly crosslinked cyclic compound does not define the volume.

The cage structure of the invention is characterized in that it is constructed of 11 or more carbon atoms. The cage structure is preferably constructed of from 11 to 30 carbon atoms, more preferably from 12 to 20 carbon atoms, and further preferably from 12 to 14 carbon atoms. When the number of carbon atoms is 11 or more, sufficient dielectric constant characteristics are obtained.

With respect to the carbon atoms as referred to herein, carbon atoms of a connecting group or a substituent substituted in the cage structure are not included. For example, it is considered that 1-methyladamantane is constructed of 10 carbon atoms.

The compound containing a cage structure of the invention is preferably a saturated aliphatic hydrocarbon, and examples thereof include diamantane, triamantane, tetramantane, and dodecahedrane. Of these, diamantane is especially preferable in view of low dielectric constant, good solubility in a coating solvent, and suppression of the generation of depositions in an insulating film.

The cage structure in the invention may have one or more substituents. Example of the substituent include —Si(A$_m$)-(X)$_{(3-m)}$ (wherein m represents an integer of from 0 to 2; and A and X are synonymous with those in the formula (1)), a halogen atom (for example, a fluorine atom, a chlorine atom, a bromine atom, and an iodine atom), a linear, branched or cyclic alkyl group having from 1 to 10 carbon atoms (for example, methyl, t-butyl, cyclopentyl, and cyclohexyl), an alkenyl group having from 2 to 10 carbon atoms (for example, vinyl and propenyl), an alkynyl group having from 2 to 10 carbon atoms (for example, ethynyl and phenylethynyl), an aryl group having from 6 to 20 carbon atoms (for example, phenyl, 1-naphthyl, and 2-naphthyl), an acyl group having from 2 to 10 carbon atoms (for example, benzoyl), an aryloxy group having from 6 to 20 carbon atoms (for example, phenoxy), an arylsulfonyl group having from 6 to 20 carbon atoms (for example, phenylsulfonyl), a nitro group, a cyano group, and a silyl group (for example, triethoxysilyl, methyldiethoxysilyl, and trivinylsilyl). Of these substituents, a fluorine atom, a bromine atom, a linear, branched or cyclic alkyl group having from 1 to 5 carbon atoms, an alkenyl group having from 2 to 5 carbon atoms, an alkynyl group having from 2 to 5 carbon atoms, and a silyl group are preferable. These substituents may be further substituted with another substituent.

The cage structure in the invention is preferably from divalent to tetravalent, more preferably divalent or trivalent, and especially preferably divalent.

The bonding of the cage structure-containing group as A to the silicon atom can be achieved at an arbitrary position of the cage structure-containing group so far as the effects of the invention are not adversely affected.

It is preferable that the number of carbon atoms constituting a group which connects the cage structure to the silicon atom (the number of carbon atoms on the shortest passage exclusive of a substituent) is not more than 6; and it is especially preferably that the cage structure is bonded directly to the silicon atom.

Examples of the hydrolyzable group as X include a halogen atom, an alkoxy group, an aryloxy group, an acyloxy group, and a silyloxy group. X is preferably a substituted or unsubstituted alkoxy group (for example, a methoxy group, an ethoxy group, a propoxy group, a butoxy group, and a methoxy-ethoxy group).

In the case of n=2 or 3, plural A's may represent the same or different group. In the case of n=1 or 2, plural X's may represent the same or different group.

As the compound represented by the formula (1), compounds represented by the following formulae are preferable. In the following formulae, X represents an alkoxy-group.

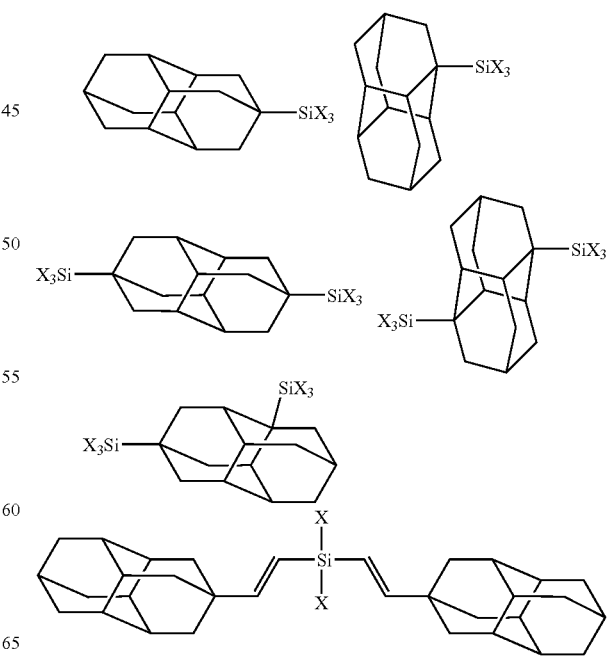

Also, a compound represented by the following general formula (2) is preferable.

In the general formula (2), $X^1$ represents a hydrolyzable group; $R^1$ represents an alkyl group, an aryl group, or a heterocyclic group; $n_1$ represents an integer of from 1 to 3; $m_1$ represents an integer of 2 or more; $L^1$ represents a divalent connecting group; and A represents a group containing a cage structure formed by 11 or more carbon atoms.

Examples of the hydrolyzable group as $X^1$ include a halogen atom, an alkoxy group, an aryloxy group, an acyloxy group, a silyloxy group, and a hydroxyl group. $X^1$ is preferably a substituted or unsubstituted alkoxy group (for example, a methoxy group, an ethoxy group, a propoxy group, a butoxy group, and a methoxyethoxy group).

$R^1$ represents a hydrogen atom, an alkyl group, an aryl group, or a heterocyclic group. Preferred examples of the alkyl group represented by $R^1$ include a linear, branched or cyclic alkyl group (for example, an alkyl group having from 1 to 20 carbon atoms, and preferably, a methyl group, an ethyl group, an isopropyl group, an n-butyl group, a 2-ethylhexyl group, an n-decyl group, a cyclopropyl group, a cyclohexyl group, and a cyclododecyl group); preferred examples of the aryl group represented by $R^1$ include a substituted or unsubstituted phenyl group or naphthyl group having from 6 to 20 carbon atoms; and preferred examples of the heterocyclic group represented by $R^1$ include a substituted or unsubstituted hetero 6-membered ring (for example, a pyridyl group, a morpholino group, and a tetrahydropyranyl group) and a substituted or unsubstituted hetero 5-membered ring (for example, a furyl group, a thiophene group, and a 1,3-dioxolan-2-yl group).

In the case of $n_1=2$ or 3, plural $X^1$'s may represent the same or different group. In the case of $n_1=1$, plural $R^1$'s may represent the same or different group.

$L^1$ represents a divalent connecting group. Examples of the connecting group include an alkylene group, an alkenylene group, an arylene group, —O—, —S—, —CO—, —NR'— (wherein R' represents a hydrogen atom, an alkyl group, or an aryl group), and a connecting group comprising a combination of two or more of these groups. Of these connecting groups, an alkylene group and an alkenylene group are preferable; and an ethylene group and a vinylene group are especially preferable.

When A represents diamantane, $m_1$ is preferably from 2 to 4; and when A represents triamantane, $m_1$ is preferably from 2 to 6.

As the compound represented by the general formula (2), a compound represented by the general formula (3) is preferable.

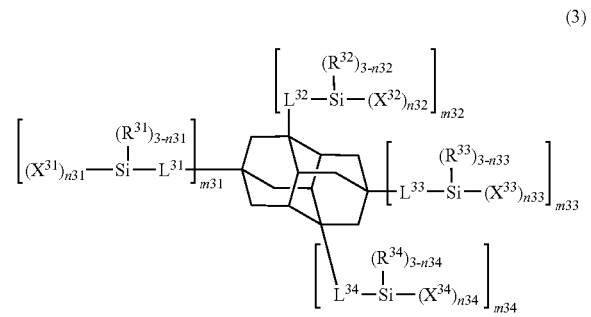

In the general formula (3), $X^{31}$ to $X^{34}$ each independently represents a hydrolyzable group; $R^{31}$ to $R^{34}$ each independently represents an alkyl group, an aryl group, or a heterocyclic group; $n_{31}$ to $n_{34}$ each independently represents an integer of from 1 to 3; $(m_{31}+m_{32}+m_{33}+m_{34})$ represents an integer of from 1 to 4; and $L^{31}$ to $L^{34}$ each represents alkylene, vinylene, arylene, —O—, —S—, —CO—, —NR'— (wherein R' represents a hydrogen atom, an alkyl group, or an aryl group), or a divalent group comprising a combination of these groups.

The hydrolyzable group represented by $X^{31}$ to $X^{34}$ is synonymous with that represented by $X^1$, and a preferred embodiment thereof is also identical.

The alkyl group, aryl group or heterocyclic group represented by $R^{31}$ to $R^{34}$ is synonymous with that represented by $R^1$, and a preferred embodiment thereof is also identical.

Specific examples of the compound represented by the general formula (2) will be given below, but it should not be construed that the invention is limited thereto.

2-1

2-2

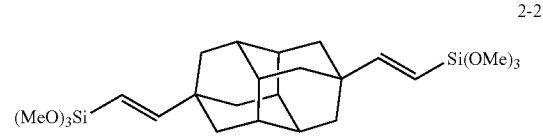

2-3

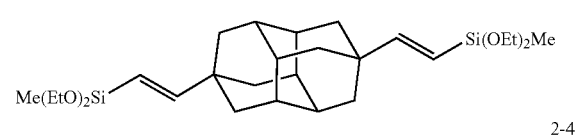

2-4

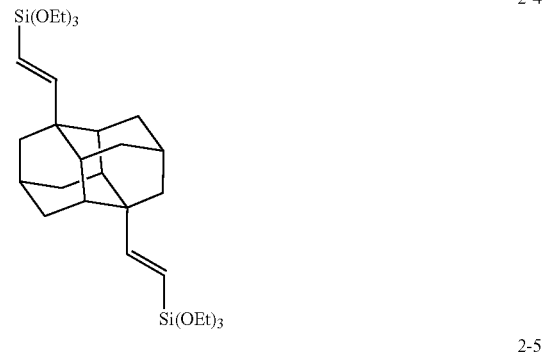

2-5

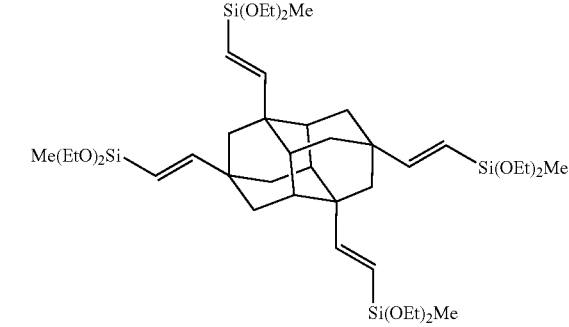

-continued 2-6

2-7

2-8
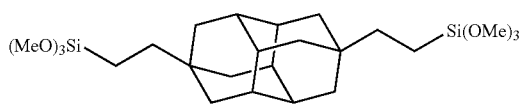

2-9
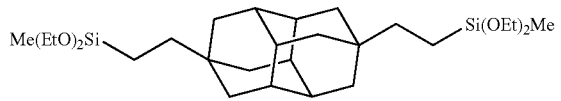

2-10
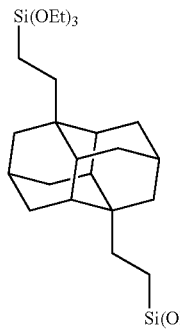

2-11
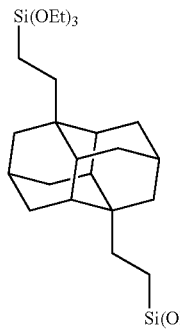

A molecular weight of the compound represented by the general formula (1) (silane compound (1)) is generally from 250 to 1,000, and preferably from 280 to 700.

A molecular weight of the compound represented by the general formula (2) (silane compound (2)) is generally from 400 to 2,000, and preferably from 450 to 1,500.

The silane compound (1) or (2) can be easily prepared by techniques well known in the silicon chemistry. For example, the silane compound (1) or (2) can be easily synthesized by a hydrosilylation reaction of adding a corresponding silane compound to a compound containing a corresponding unsaturated group in the presence of a transition metal complex catalyst or a reaction of a cage structure-containing halogenated compound with a Grignard reagent.

In the composition for forming an insulating film of the invention, these silane compounds may be used singly or in combinations of two or more kinds thereof.

Also, a known silicon compound to be added in the composition for forming an insulating film (for example, tetramethoxysilane, tetraethoxysilane, methyltrimethoxysilane, and methyltriethoxysilane) may be used together with the silane compound (1) or (2).

Examples of other silane compounds which may be added as need arises for the purpose of enhancing the film characteristics of a material include an organosilicon compound represented by the following general formula (A) or a polymer constructed of such a compound as a monomer.

$$(R_a)_q\text{—Si—}(OR_b)_{4-q} \quad (A)$$

In the general formula (A), $R_a$ represents an alkyl group, an aryl group, or a heterocyclic group; and $R_b$ represents a hydrogen atom, an alkyl group, an aryl group, or a silyl group. These groups may further have a substituent.

q represents an integer of from 0 to 4; and when q or (4-q) is 2 or more, $R_a$'s or $R_b$'s may be each the same or different. Also, the subject compounds may be connected to each other via the substituent of $R_a$ or $R_b$ to form a polymer.

q is preferably from 0 to 2; and $R_b$ is preferably an alkyl group. Further, when q is 0, preferred examples of the compound include tetramethoxysilane (TMOS) and tetraethoxysilane (TEOS); and when q is 1 or 2, preferred examples of the compound include the following compounds.

(A-1) Me—Si(OEt)$_3$ (A-2) Me—Si(OMe)$_3$ (A-3) n-C$_3$H$_7$—Si—(OEt)$_3$ (A-4) n-C$_6$H$_{13}$—Si—(OEt)$_3$ (A-5) 

(A-6) 

(A-7) (EtO)$_3$—Si—(CH$_2$)$_2$—Si—(OEt)$_3$ (A-8) Me(EtO)$_2$—Si—(CH$_2$)$_2$—Si—(OEt)$_2$Me

In the case of using other silane compound such as the compound represented by the general formula (A) jointly, such other silane compound is preferably used in an amount in the range of from 1 to 200% by mole, and more preferably from 10 to 100% by mole based on the silane compound (1) and/or (2).

The foregoing silane compound (1) and/or (2) and optionally other silane compound are hydrolyzed and condensed to obtain a silicon oxygen crosslinked compound. The silicon oxygen crosslinked structure as referred to herein means a crosslinked structure comprising a siloxane bond (–(Si—O)$_n$–) as formed itself by condensation.

In hydrolyzing and condensing the silane compound, water is preferably used in an amount of from 0.5 to 150 moles, and especially preferably from 1 to 100 moles based on one mole of the whole of the silane compound containing the silane compound (1) and/or (2) and optionally other silane compound. The amount of water to be added is preferably 0.5 moles or more in view of crack resistance of the film and is preferably not more than 150 moles in view of preventing the deposition or gelation of a polymer during the hydrolysis and condensation reaction.

In hydrolyzing and condensing the silane compound, it is preferred to use an alkaline catalyst, an acid catalyst, or a metal chelate compound.

Examples of the alkaline catalyst include sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, methylamine, ethylamine, propylamine, butylamine, pentylamine, hexylamine, heptylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, and 3-amino-3-methylamine. Of these, ammonia, amines, and amine salts are preferable; ammonia, organic amines, and organic amine salts are especially preferable; and ammonia, alkylamines, and tetraalkylammonium hydroxides are the most preferable. These alkaline catalysts may be used singly, or two or more kinds thereof may be used simultaneously.

As the acid catalyst, inorganic or organic protonic acids are preferable. Examples of the inorganic protonic acid include hydrochloric acid, sulfuric acid, hydrofluoric acid, phosphoric acids (for example, $H_3PO_4$, $H_3PO_3$, $H_4P_2O_7$, $H_5P_3O_{10}$, metaphosphoric acid, and hexafluorophosphoric acid), boric acid, nitric acid, perchloric acid, tetrafluoroboric acid, and hexafluoroarcenic acid, hydrobromic acid, and solid acids such as tungstophosphoric acid and tungsten peroxo complexes.

Examples of the organic protonic acid include low molecular compounds such as carboxylic acids (for example, oxalic acid, acetic acid, propionic acid, butanoic acid, pentanoic acid, hexanoic acid, heptanoic acid, octanoic acid, nonanoic acid, decanoic acid, maleic acid, methylmalonic acid, adipic acid, sebacic acid, gallic acid, butyric acid, mellitic acid, arachidic acid, shikimic acid, 2-ethylhexanoic acid, oleic acid, stearic acid, lonolic acid, linoleic acid, salicylic acid, monochloroacetic acid, dichloroacetic acid, trichloroacetic acid, p-aminobenzoic acid, formic acid, malonic acid, phthalic acid, fumaric acid, citric acid, tartaric acid, succinic acid, fumaric acid, itaconic acid, mesaconic acid, citraconic acid, malic acid, a hydrolysate of glutaric acid, a hydrolysate of maleic anhydride, a hydrolysate of phthalic anhydride, trifluoroacetic acid, benzoic acid, and substituted benzoic acids), phosphoric esters (for example, those having from 1 to 30 carbon atoms, such as methyl phosphate, propyl phosphate, dodecyl phosphate, phenyl phosphate, dimethyl phosphate, and didodecyl phosphate), phosphorous esters (for example, those having from 1 to 30 carbon atoms, such as methyl phosphite, dodecyl phosphite, diethyl phosphite, diisopropyl phosphite, and didodecyl phosphite), sulfonic acids (for example, those having from 1 to 15 carbon atoms, such as benzenesulfonic acid, toluenesulfonic acid, hexafluorobenzenesulfonic acid, trifluoromethanesulfonic acid, and dodecylsulfonic acid), carboxylic acids (for example, oxalic acid, acetic acid, trifluoroacetic acid, benzoic acid, and substituted benzoic acids), imides (for example, bis(trifluoromethanesulfonyl)imide acid and trifluoromethanesulfonyl trifluoroacetamide), and phosphonic acids (for example, those having from 1 to 30 carbon atoms, such as methylphosphonic acid, ethylphosphonic acid, phenylphosphonic acid, diphenylphosphonic acid, and 1,5-naphthalenebisphosphonic acid); and high molecular compounds containing a protonic acid site, such as perfluorocarbon sulfonic acid polymers represented by Nafion, poly(meth)acrylates containing a phosphoric acid group in the side chains thereof (JP-A-2001-114834), sulfonated polyetheretherketones (JP-A-6-93111), sulfonated polyethersulfones (JP-A-10-45913), and sulfonated polysulfones (JP-A-9-245818).

Examples of the metal chelate compound include titanium chelate compounds such as triethoxy mono(acetylacetonato) titnanium, tri-n-propoxy mono(acetylacetonato)titanium, tri-isopropoxy mono(acetylacetonato)titanium, tri-n-butoxy mono(acetylacetonato)titanium, tri-sec-butoxy mono(acetylacetonato)titanium, tri-t-butoxy mono(acetylacetonato)titanium, diethoxy bis(acetylacetonato)titanium, di-n-propoxy bis(acetylacetonato)titanium, diisopropoxy bis(acetylacetonato)titanium, di-n-butoxy bis(acetylacetonato)titanium, di-sec-butoxy bis(acetylacetonato)titanium, di-t-butoxy bis(acetylacetonato)titanium, monoethoxy tris(acetylacetonato)titanium, mono-n-propoxy tris(acetylacetonato)titanium, monoisopropoxy tris(acetylacetonato)titanium, mono-n-butoxy tris(acetylacetonato)titanium, mono-sec-butoxy tris(acetylacetonato)titanium, mono-n-butoxy tris(acetylacetonato)titanium, tetrakis(acetylacetonato)titanium, triethoxy mono(ethylacetoacetato)titanium, tri-n-propoxy mono(ethylacetoacetato)titanium, triisopropoxy mono(ethylacetoacetato)titanium, tri-n-butoxy mono(ethylacetoacetato)titanium, tri-sec-butoxy mono(ethylacetoacetato)titanium, tri-t-butoxy mono(ethylacetoacetato)titanium, diethoxy bis(ethylacetoacetato)titanium, di-n-propoxy bis(ethylacetoacetato)titanium, diisopropoxy bis(ethylacetoacetato)titanium, di-n-butoxy bis(ethylacetoacetato)titanium, di-sec-butoxy bis(ethylacetoacetato)titanium, di-t-butoxy bis(ethylacetoacetato)titanium, monoethoxy tris(ethylacetoacetato)titanium, mono-n-propoxy tris(ethylacetoacetato)titanium, monoisopropoxy tris(ethylacetoacetato)titanium, mono-n-butoxy tris(ethylacetoacetato)titanium, mono-sec-butoxy tris(ethylacetoacetato)titanium, mono-t-butoxy tris(ethylacetoacetato)titanium, tetrakis(ethylacetoacetato)titanium, mono(acetylacetonato)tris(ethylacetoacetato)titanium, bis(acetylacetonato)bis(ethylacetoacetato)titanium, and tris(acetylacetonato)mono(ethylacetoacetato)titanium; zirconium chelate compounds such as triethoxy mono(acetylacetonato)zirconium, tri-n-propoxy mono(acetylacetonato)zirconium, triisopropoxy mono(acetylacetonato)zirconium, tri-n-butoxy mono(acetylacetonato)zirconium, tri-sec-butoxy mono(acetylacetonato)zirconium, tri-t-butoxy mono(acetylacetonato)zirconium, diethoxy bis(acetylacetonato)zirconium, di-n-propxy bis(acetylacetonato)zirconium, diisopropoxy bis(acetylacetonato)zirconium, di-n-butoxy bis(acetylacetonato)zirconium, di-sec-butoxy bis(acetylacetonato)zirconium, di-t-butoxy bis(acetylacetonato)zirconium, monoethoxy tris(aetylacetonato)zirconium, mono-n-propoxy tris(aetylacetonato)zirconium, monoisopropoxy tris(aetylacetonato)zirconium, mono-n-butoxy tris(aetylacetonato)zirconium, mono-sec-butoxy tris(aetylacetonato)zirconium, mono-t-butoxy tris(aetylacetonato)zirconium, tetrakis(aetylacetonato)zirconium, triethoxy mono(ethylacetoacetato)zirconium, tri-n-propoxy mono(ethylacetoacetato)zirconium, triisopropoxy mono(ethylacetoacetato)zirconium, tri-n-butoxy mono(ethylacetoacetato)zirconium, tri-sec-butoxy mono(ethylacetoacetato)zirconium, tri-t-butoxy mono(ethylacetoacetato)zirconium, diethoxy bis(ethylacetoacetato)zirconium, di-n-propxy bis(ethylacetoacetato)zirconium, diisopropxy bis(ethylacetoacetato)zirconium, di-n-butoxy bis(ethylacetoacetato)zirconium, di-sec-butoxy bis(ethylacetoacetato)zirconium, di-t-butoxy bis(ethylacetoacetato)zirconium, monoethoxy tris(ethylacetoacetato)zirconium, mono-n-propoxy tris(ethylacetoacetato)zirconium, monoisopropoxy tris(ethylacetoacetato)zirconium, mono-n-butoxy tris(ethylacetoacetato)zirconium, mono-sec-butoxy tris(ethylacetoacetato)zirconium, mono-t-butoxy tris(ethylacetoacetato)zirconium, tetrakis(ethylacetoacetato)zirconium, mono(acetylacetonato)tris(ethylacetoacetato)zirconium, bis(acetylacetonato) bis(ethylacetoacetato)zirconium, and tris(acetylacetonato) mono(ethylacetoacetato)zirconium; and aluminum chelate compounds such as tris(acetylacetonato)aluminum and tris(ethylacetoacetato)aluminum. Of these, titanium or aluminum chelate compounds are preferable; and titanium chelate compounds are especially preferable. These metal chelate compounds may be used singly, or two or more kinds thereof may be used simultaneously.

A total amount of the catalyst and chelate compound to be used is usually from 0.00001 to 10 moles, and preferably from 0.00005 to 5 moles based on one mole of the silane compound. When the amount of the catalyst to be used falls within the foregoing range, there is less possibility that the deposition or gelation of a polymer occurs during the reaction.

The temperature at which the silane compound is hydrolyzed and condensed is usually from 0 to 100° C., and preferably from 10 to 90° C., and the time is usually from 5 minutes to 200 hours, and preferably from 15 minutes to 40 hours.

The solvent which is used in the hydrolysis and condensation is not particularly limited so far as it can dissolve the silane compound as a solute therein. Preferably, examples thereof include ketones (for example, cyclohexanone, cyclopentanone, 2-heptanone, methyl isobutyl ketone, methyl ethyl ketone, and acetone), carbonate compounds (for example, ethylene carbonate and propylene carbonate), heterocyclic compounds (for example, 3-methyl-2-oxazolidinone, dimethylimidazolidinone, and N-methylpyrrolidone), cyclic ethers (for example, dioxane and tetrahydrofuran), chain ethers (for example, diethyl ether, ethylene glycol dimethyl ether, propylene glycol dimethyl ether, tetraethylene glycol dimethyl ether, and polyethylene glycol dimethyl ether), alcohols (for example, methanol, ethanol, isopropanol, ethylene glycol monomethyl ether, ethylene glycol monoethyl ether, propylene monomethyl ether (PGME), triethylene glycol monobutyl ether, propylene glycol monopropyl ether, and triethylene glycol monomethyl ether), polyhydric alcohols (for example, ethylene glycol, propylene glycol, polyethylene glycol, polypropylene glycol, and glycerin), nitrile compounds (for example, acetonitrile, glutarodinitrile, methoxyacetonitrile, propionitrile, and benzonitrile), esters (for example, ethyl acetate, butyl acetate, methyl lactate, ethyl lactate, methyl methoxypropionate, ethyl ethoxypropionate, methylpyruvate, ethyl puruvate, propyl pyruvate, 2-methoxyethyl acetate, ethylene glycol monoethyl ether acetate, propylene glycol monomethyl ether acetate (PGMEA), γ-butyrolactone, phosphoric esters, and phosphonic esters), aprotic polar substances (for example, dimethyl sulfoxide, sulfolane, N,N-dimethylformamide, and dimethylacetamide), non-polar solvents (for example, toluene, xylene, and mesitylene), chlorine based solvents (for example, methylene dichloride and ethylene dichloride), diisopropylbenzene, and water.

Of these, alcohols such as propylene glycol monopropyl ether and propylene glycol monomethyl ether; esters such as propylene glycol monomethyl ether acetate (PGMEA); esters such as γ-butyrolactone; carbonates such as ethylene carbonate; ketones such as cyclohexanone; aprotic polar substances; cyclic ethers such as tetrahydrofuran; non-polar solvents; and water are preferable. These solvents may be used singly or in admixture of two or more kinds thereof.

Preferred example of the solvent include propylene glycol monomethyl ether acetate, propylene glycol monomethyl ether, 2-heptanone, cyclohexanone, γ-butyrolactone, ethylene glycol monomethyl ether, ethylene glycol monoethyl ether, ethylene glycol monoethyl ether acetate, propylene glycol monomethyl ether, propylene glycol monoethyl ether, ethylene carbonate, butyl acetate, methyl lactate, ethyl lactate, methyl methoxypropionate, ethyl ethoxypropionate, N-methylpyrrolidone, N,N-dimethylformamide, tetrahydrofuran, methyl isobutyl ketone, xylene, mesitylene, and diisopropylbenzene.

Composition

The composition of the invention is usually prepared by dissolving at least one of the silane compound itself and the above-prepared hydrolysate and condensate of the subject silane compound in solvent such as organic solvents as enumerated as the solvent to be used for the hydrolysis and condensation, if desired and water. The solvent at the time of preparing this composition may be the same as or different from the solvent to be used for the hydrolysis and condensation.

A concentration of the whole solids of the composition of the invention is preferably from 2 to 30% by weight and is properly adjusted depending upon the object for use. When the concentration of the whole solids of the composition is from 2 to 30% by weight, the thickness of the coating film is in a suitable range, and the storage stability of the composition is more excellent.

By coating the composition of the invention and then drying, preferably heating, it is possible to form a good insulating material. In particular, it is possible to provide a good insulating film.

In coating the composition of the invention on a substrate such as silicon wafers, $SiO_2$ wafers, and SiN wafers, coating means such as dipping, roll coating, and spraying can be employed.

With respect to the film thickness, a coating film having a dry thickness of from about 0.05 to 1.5 μm by single coating and from about 0.1 to 3 μm by double coating can be formed. Thereafter, by drying the coating film at the ambient temperature or heating it at a temperature of from about 80 to 600° C. usually for from about 5 to 240 minutes, it is possible to form an insulating film made of a vitreous or giant molecule or a mixture thereof. For the heating, a hot plate, an oven, a furnace, and the like can be used. With respect to the heating atmosphere, the heating can be carried out under atmospheric pressure, in a nitrogen atmosphere or an argon atmosphere, in vacuo, or under a reduced pressure where the oxygen concentration is controlled.

More specifically, a low dielectric constant insulating film can be formed by coating the composition of the invention on a substrate (usually a metallic wiring-containing substrate) by, for example, the spin coating method; undergoing a first thermal treatment at a temperature of not higher than 300° C., thereby not only drying the solvent but also crosslinking the siloxane as contained in the composition; and then undergoing a second thermal treatment (annealing) at a temperature of high than 300° C. and not higher than 450° C. (preferably from 330 to 400° C.) generally for from one minute to 10 hours.

In the composition of the invention, a pore forming agent such as a thermally decomposable compound may be added. Examples of the pore forming agent include via hole generators described in JP-T-2002-530505.

On the insulating film formed of the composition of the invention, a separate insulating film such as a silicon oxide film may be formed by, for example, the chemical vapor deposition method. This is effective for blocking the insulating film formed by the invention from the air outside and suppressing a reduction of hydrogen and fluorine remaining in the film. Further, this separate insulating film is also effective for preventing the insulating film by the invention from damaging in treatments in subsequent steps (for example, a flattening treatment by CMP).

EXAMPLES

The invention will be hereunder described in more detail with reference to the Examples, but it should not be construed that the invention is limited to these Examples.

Synthesis Example 1

Synthesis of diamantyltriethoxysilane

A catalytic amount of iodine was added to a solution of 1.5 g (62 mmoles) of magnesium, 45 mL (200 mmoles) of tetraethoxysilane (TEOS) and 30 mL of dibutyl ether, and the mixture was heated at 60° C. In the resulting mixture, 11.0 g (41 mmoles) of 4-bromodiamantane dissolved in 50 mL of dibutyl ether was dropped, and the resulting solution was filtered. The filtrate was subjected to evaporation by a rotary evaporator, thereby eliminating the dibutyl ether and TEOS, and the remaining filtrate was dissolved in benzene. The solution was further lyophilized, thereby obtaining 10.5 g (30 mmoles) of desired diamantyltriethoxysilane.

Example 1

Preparation of Insulating Film and Measurement of Dielectric Constant

In a flask equipped with a stirrer, a thermometer and a dropping funnel, 20 mmoles of diamantyltriethoxysilane as prepared in the foregoing Synthesis Example 1 was dissolved in cyclohexanone, thereby preparing a 20% by weight solution. An aqueous solution of 60 mmoles of nitric acid (concentration: 200 ppm) was dropped in the flask, and the inside of the reaction system was heated at 60° C. and stirred for 2 hours. After cooling the solution within the flask to room temperature, the stirring was stopped, and the resulting mixture was concentrated in vacuo to remove water, followed by filtration.

The thus prepared diamantyltriethoxysilane-containing coating solution was spin coated in a thickness of 4,000 angstroms on a silicon substrate and dried on a hot plate at 150° C. for one minute to remove the solvent. Next, the silicon substrate after drying was transferred into a clean oven and subjected to a thermal treatment in nitrogen having an oxygen concentration of not more than 10 ppm at 400° C. for 30 minutes. There was thus obtained a desired insulating film.

After allowing the insulating film to stand for 24 hours under conditions at a temperature of 24° C. and a humidity of 50%, a relative dielectric constant of the insulating film was measured at 1 MHz by using a mercury probe manufactured by Four Dimension and an LCR meter HP4285A, manufactured by Hewlett-Packard and found to be 2.3.

Comparative Example 1

Preparation of Insulating Film and Measurement of Dielectric Constant

For comparison, using adamantyltriethoxysilane, the test was carried out under the same conditions as in Example 1. As a result, the relative dielectric constant was found to be 2.5.

Synthesis Example 2

Synthesis of Compound 2-1

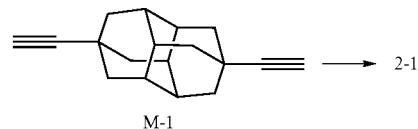

Compound M-1 (4.7 g) and 20 µL of a xylene solution of a platinum(0)-1,3-divinyl-1,1,3,3-tetramethyldisiloxane complex (manufactured by Aldrich) were dissolved in 25 mL of toluene in a nitrogen gas stream, and the solution was heated at 80° C. Triethoxysilane (8.3 g) was gradually dropped therein while taking care of heat generation. After completion of the dropping, the mixture was allowed to react at the same temperature for additional one hour, and the reaction mixture was concentrated and purified by silica gel column chromatography, thereby obtaining 7.4 g of Compound 2-1 (white crystal).

Synthesis Example 3

Synthesis of Compound 2-3

6.5 g of Compound 2-3 (white crystal) was obtained in the same manner as in Synthesis Example 2, except for using 6.7 g of diethoxymethylsilane in place of the triethoxysilane.

Synthesis Example 4

Synthesis of Compound 2-7

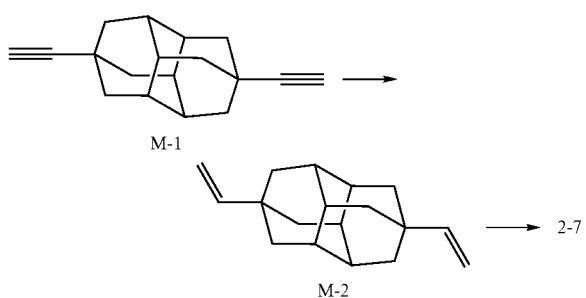

Synthesis of Compound (M-2)

Compound M-1 (11 g) was suspended in 50 mL of toluene in a nitrogen gas stream, and the suspension was cooled with ice water. 100 mL of a 1M dibutylaluminum solution in hexane was added to the mixture. After completion of the addition, the ice water was removed. The reaction mixture rose to 30° C. and became a uniform solution, and a white precipitate was then generated. After stirring at room temperature for 3 hours, the reaction mixture was gradually added to 200 mL of a saturated ammonium chloride aqueous solution. The mixture was filtered by a celite, and the filtrate was extracted with ethyl acetate. An organic layer was dried over magnesium sulfate, and the solvent was distilled off in vacuo. The residue was purified by silica gel column chromatography, thereby obtaining 8.9 g of Compound M-2 (white crystal).

Synthesis of Compound 2-7

Compound M-2 (2.0 g) and 20 μL of a xylene solution of a platinum(0)-1,3-divinyl-1,1,3,3-tetramethyldisiloxane complex (manufactured by Aldrich) were dissolved in 10 mL of toluene in a nitrogen gas stream, and the solution was heated at 80° C. Triethoxysilane (3.3 g) was gradually dropped therein while taking care of heat generation. After completion of the dropping, the mixture was allowed to react at the same temperature for additional one hour, and the reaction mixture was concentrated and purified by silica gel column chromatography, thereby obtaining 3.2 g of Compound 2-7 (white crystal).

Synthesis Example 5

Synthesis of Compound 2-9

3.5 g of Compound 2-9 (white crystal) was obtained in the same manner as in Synthesis Example 4, except for using diethoxymethylsilane (2.7 g) in place of the triethoxysilane.

Example 2

Preparation of Coating Liquid

In a solution of Compound 2-1 (4.4 g) as prepared in Synthesis Example 2 dissolved in 17.6 g of propylene glycol monomethyl ether (PGME), 0.6 mL of water having 7 mg of 70% nitric acid dissolved therein was dropped, and the reaction mixture was stirred at room temperature for 5 hours. Thereafter, the stirring was stopped, and the resulting reaction mixture was concentrated in vacuo to remove low-boiling substances and water, followed by filtration. To this solution, 11 g of PGME was added, thereby preparing a coating liquid.

Example 3

Preparation of Coating Liquid

In a solution of Compound 2-3 (4 g) as prepared in Synthesis Example 3 dissolved in 16 g of propylene glycol monomethyl ether (PGME), 0.6 mL of water having 7 mg of 70% nitric acid dissolved therein was dropped, and the reaction mixture was stirred at room temperature for 5 hours. Thereafter, the stirring was stopped, and the resulting reaction mixture was concentrated in vacuo to remove low-boiling substances and water, followed by filtration. To this solution, 11 g of propylene glycol monomethyl ether acetate (PGMEA) was added, thereby preparing a coating liquid.

Example 4

Preparation of Coating Liquid

In a solution of Compound 2-7 (4.5 g) as prepared in Synthesis Example 4 dissolved in 18 g of propylene glycol monomethyl ether (PGME), 0.6 mL of water having 7 mg of 70% nitric acid dissolved therein was dropped, and the reaction mixture was stirred at room temperature for 5 hours. Thereafter, the stirring was stopped, and the resulting reaction mixture was concentrated in vacuo to remove low-boiling substances and water, followed by filtration. To this solution, 11 g of propylene glycol monomethyl ether acetate (PGMEA) was added, thereby preparing a coating liquid.

Example 5

Preparation of Coating Liquid

In a solution of Compound 2-9 (4 g) as prepared in Synthesis Example 5 dissolved in 16 g of propylene glycol monopropyl ether (PGP), 0.6 mL of water having 7 mg of 70% nitric acid dissolved therein was dropped, and the reaction mixture was stirred at room temperature for 5 hours. Thereafter, the stirring was stopped, and the resulting reaction mixture was concentrated in vacuo to remove low-boiling substances and water, followed by filtration. To this solution, 11 g of PGME was added, thereby preparing a coating liquid.

Example 6

Preparation of Coating Liquid

In a solution of Compound 2-3 (3 g) and TEOS (1 g) dissolved in 16 g of PGME, 0.77 mL of water having 9.7 mg of 70% nitric acid dissolved therein was dropped, and the reaction mixture was stirred at room temperature for 5 hours. Thereafter, the stirring was stopped, and the resulting reaction mixture was concentrated in vacuo to remove low-boiling substances and water, followed by filtration. To this solution, 8 g of PGP was added, thereby preparing a coating liquid.

Preparation of Insulating Film and Measurement of Dielectric Constant

Each of the thus prepared coating liquids was spin coated in a thickness of 4,000 angstroms on a silicon substrate and dried on a hot plate at 150° C. for one minute to remove the solvent. Next, the silicon substrate after drying was transferred into a clean oven and subjected to a thermal treatment in nitrogen having an oxygen concentration of not more than 10 ppm at 400° C. for 30 minutes. There are thus obtained desired insulating films.

After allowing each of the insulating films to stand for 24 hours under conditions at a temperature of 24° C. and a humidity of 50%, a relative dielectric constant of the insulating film was measured at 1 MHz by using a mercury probe manufactured by Four Dimension and an LCR meter HP4285A, manufactured by Hewlett-Packard.

The measurement results of the relative dielectric constant are shown in Table 1 along with the results of the preceding Example 1 and Comparative Example 1.

TABLE 1

| | Relative dielectric constant |
|---|---|
| Example 1 | 2.3 |
| Example 2 | 2.2 |
| Example 3 | 2.1 |
| Example 4 | 2.1 |
| Example 5 | 2.0 |
| Example 6 | 2.3 |
| Comparative Example 1 | 2.5 |

It is noted that the insulating films according to the Examples of the invention have a low dielectric constant.

According to the invention, a novel composition for forming an insulating film capable of forming an insulating film having a low relative dielectric constant of not more than 2.4 and having high reliability, which is free from defects caused due to moisture absorption, etc. In particular, the invention can contribute to an improvement of response speed of semiconductor units having a multilayered wiring structure.

The entire disclosure of each and every foreign patent application from which the benefit of foreign priority has been claimed in the present application is incorporated herein by reference, as if fully set forth.

What is claimed is:

1. An insulating material formed by using a composition comprising:
    (a) a compound represented by formula (3):

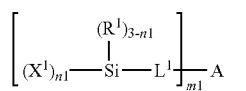 (2)

wherein (m31+m32+m33+m34) represents an integer of from 1 to 4;

n31 to n34 each independently represents an integer of from 1 to 3;

$X^{31}$ to $X^{34}$ each independently represents a hydrolyzable group;

$R^{31}$ to $R^{34}$ each independently represents an alkyl group, an aryl group or a heterocyclic group;

$L^{31}$ to $L^{34}$ each independently represents an alkylene, a vinylene, an arylene, —O—, —S—, —CO—, —NR'— or a divalent group including a combination thereof; and R' represents a hydrogen atom, an alkyl group or an aryl group;

(b) at least one of a hydrolysate of the compound represented by formula (3) and a condensate of the compound represented by formula (3); and (c) at least one of an organic solvent and water.

2. An insulating film formed by using a composition according to claim 1.

3. The insulating material according to claim 1, wherein the hydrolyzable group represented by $X^{31}$ to $X^{34}$ is selected from the group consisting of a halogen atom, an alkoxy group, an aryloxy group, an acyloxy group, a silyloxy group and a hydroxyl group.

4. The insulating material according to claim 3, wherein the hydrolyzable group represented by $X^{31}$ to $X^{34}$ is a substituted or unsubstituted alkoxy group.

5. The insulating material according to claim 1, wherein $R^{31}$ to $R^{34}$ each independently represents a linear, branched or cyclic alkyl group, a substituted or unsubstituted phenyl group or naphthyl group, a substituted or unsubstituted hetero 6-membered ring or a substituted or unsubstituted hetero 5-membered ring.

* * * * *